United States Patent [19]
Fong et al.

[11] Patent Number: 5,179,173
[45] Date of Patent: Jan. 12, 1993

[54] AMINOALKYLPHOSPHINATES AND PHOSPHINIC ACID-CONTAINING POLYMERS THEREFROM

[75] Inventors: Dodd W. Fong, Naperville; Mary A. Kinsella, Manhattan; James F. Kneller, LaGrange Park; John W. Sparapany, Bolingbrook, all of Ill.

[73] Assignee: Nalco Chemical Company, Naperville, Ill.

[21] Appl. No.: 683,008

[22] Filed: Apr. 10, 1991

[51] Int. Cl.$^5$ .................................. C08F 8/40
[52] U.S. Cl. ............... 525/329.4; 525/329.8; 525/330.4; 525/340
[58] Field of Search ............... 525/329.4, 329.8, 330.4

[56] References Cited

U.S. PATENT DOCUMENTS

| | | | |
|---|---|---|---|
| 3,449,308 | 6/1969 | Blatz | 525/329.8 |
| 4,590,014 | 5/1986 | Wolf et al. | |
| 4,598,092 | 7/1986 | Sasaki et al. | |
| 4,604,431 | 8/1986 | Fong et al. | |
| 4,678,840 | 7/1987 | Fong et al. | |

Primary Examiner—Bernard Lipman
Attorney, Agent, or Firm—Robert A. Miller; John G. Premo

[57] ABSTRACT

The invention describes novel amino(lower alkyl)phosphinic acid compounds and their use to modify acrylamide polymers, acrylic acid polymers and acrylamide-acrylic acid co-polymers which produces polymers containing amidoalkylphosphinic acid groups.

6 Claims, No Drawings

AMINOALKYLPHOSPHINATES AND PHOSPHINIC ACID-CONTAINING POLYMERS THEREFROM

INTRODUCTION

The present invention relates to aminoalkylphosphinates and phosphinic acid-containing polymers made therefrom.

THE INVENTION

This invention is directed to certain novel $C_2$–$C_6$ aminoalkylphosphinic acids and salts thereof.

The invention also relates to low molecular weight acrylamide polymers and co-polymers of acrylic acid with acrylamide which have been modified to incorporate within their structure the $C_2$–$C_6$ amidoalkylphosphinic acid groups and the alkali metal, ammonium and amine salts thereof. The polymers of the invention are capable of preventing or reducing scale and corrosion which form on metal surfaces in contact with scale forming and/or corrosive waters.

THE AMINOALKYLPHOSPHINATES

As indicated, these compounds contain $C_2$–$C_6$ alkyl groups which may be either straight or branched chain. In a preferred embodiment these compounds contain a hydroxyl group in the alpha position.

Illustrative of such compounds are alpha-hydroxy-beta-aminoethylphosphinic acid, alpha-hydroxy-beta-aminoisopropylphosphinic acid and aminopropylphosphinic acid. Also included are their alkali metal (e.g., sodium), ammonium and amine salts such as the trimethyl amine salt.

These compounds are considered to be novel in and of themselves. They are capable of being used to introduce phosphinic acid and phosphinic acid salt groups into acrylic acid or acrylamide polymers.

The alpha-hydroxy-beta-aminoalkylphosphinic acids are conveniently prepared by the reaction of a haloalkyl-hydroxyphosphinic acid with ammonia. The starting haloalkyl-hydroxyphosphinic acids are described along with their method of preparation in U.S. Pat. No. 4,598,092, the disclosure of which is incorporated herein by reference. This patent teaches that the alpha-hydroxy-beta-haloethylphosphinic acid is an acidic substance and can be produced by reacting a haloacetaldehyde or its dialkyl acetals with aqueous phosphinic acid in the presence of an acid catalyst (e.g., hydrochloric acid, sulfuric acid), usually at a temperature of 10° to 100° C. for 1 to 24 hours. The amount of the phosphinic acid may be 1.0 to 10 equivalents to the haloacetaldehyde or its dialkylacetal. This reaction produces the compound

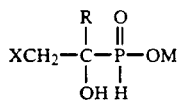

where M is H, alkali metal, ammonia or amine, X is Cl or Br and R is H or a lower alkyl group such as $CH_3$, $C_2H_5$, etc.

These compounds are then reacted with aqueous concentrated solutions of ammonium hydroxide (e.g., about 20%), which are added to a chilled polar solvent solution of alpha-hydroxy-beta-haloalkylphosphinic acids and then heated to about 30°–70° C. for about 2–10 hours. To illustrate this preparation the following is given by example.

EXAMPLE 1

A solution of

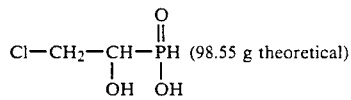

in water (165 g) was cooled to 0° C. and 30% aqueous ammonia (442 ml) was added dropwise over 20 minutes. The mixture was then heated to 55° C. for five hours.

Using the above described preparative techniques, the following compounds were prepared: alpha-hydroxy-beta-aminoethylphosphinic acid and alpha-hydroxy-beta-aminoisopropylphosphinic acid. Structures of these compounds were confirmed by NMR.

In the case of aminopropylphosphinic acid, this compound is prepared by reacting allyl amine with an alkali metal hypophosphite in the presence of a free radical catalyst. The reaction of olefinic groups with alkali metal hypophosphites to produce alkyl phosphinate salts is well known and is described in U.S. Pat. No. 4,590,014, the disclosure of which is incorporated herein by reference. The patent does not disclose the reaction of allyl amine with alkali metal hypophosphites to produce aminopropylalkali metal phosphinates. When the acid form of these salts is desired they can be prepared by treatment with dilute mineral acids or by the use of acid form cation exchange resins. The preparation of this compound is show below in Example 2.

EXAMPLE 2

Allyl amine (30 g), sodium hypophosphite (50.95 g) and azobisisobutyronitrile (AIBN, 2.16 g) in 50% aqueous methanol (200 ml) were heated to 80° C. with vigorous stirring.

Additional AIBN (2.16 g) was added portionwise over 5 minutes and the reaction was maintained at 80° C. for 6 hours.

THE STARTING ACRYLAMIDE POLYMERS AND CO-POLYMERS OF ACRYLIC ACID WITH ACRYLAMIDE

Homopolymers of acrylamide, acrylic acid and co-polymers of acrylic acid with acrylamide which are modified with the aminoalkylphosphinates should have a weight average molecular weight within the range of 1,000–100,000, preferably 1,000–40,000 and most preferably, 1,000–20,000. They are utilized in the reactions described hereafter in the form of aqueous solutions, typically having concentrations between 5%–40% by weight. When the starting polymers are acrylic acid and acrylamide co-polymers, the mole ratios may vary between 5-95 to 95-5 mole percent. Typically, however, these co-polymers will contain between 5–50 mole percent of acrylamide. The polymers may contain up to 15 mole percent of diluent monomers such as acrylonitrile, vinyl acetate, vinyl chloride and styrene.

MODIFICATION OF THE POLYMERS WITH THE AMINO($C_2$–$C_6$ ALKYL)PHOSPHINIC ACID COMPOUNDS

The reaction of the aminoalkylphosphinic acids, or their salts, converts the carboxylic acid groups of the acrylic acid polymer into the corresponding amido groups by means of a simple amidation reaction. When the polymers contain acrylamide groups, the aminoalkylphosphinic acids or their salts undergo a transamidation reaction whereby the amine is substituted for the amide nitrogen in the acrylamide polymer.

The amount of substitution of the amino groups may be as little as 1 mole percent up to about as much as 30 mole percent; typically the substitution will be between 3-20 mole percent. The reaction using the conditions described hereafter results in about a 50% conversion of the acid or amide groups to the amidoalkylphosphinates.

The reaction conditions used to either amidate the carboxylic acid or transamidate the amide groups are described in U.S. Pat. No. 4,678,840. This patent is primarily directed to transamidation reactions of aminoalkylphosphonates with acrylamide polymeric moieties contained in acrylic acid co-polymers. U.S. Pat. No. 4,604,431 discloses reaction conditions for converting acrylic acid groups into amide groups by reacting them with aminosulfonic acid groups. The reaction conditions described in this patent are used to convert a portion of the acrylic acid groups in the homo- or co-polymers of acrylic acid into amidoalkylphosphinic acid groups or their salts. These patents are incorporated herein by reference.

In conducting the reactions described above, it is beneficial that the pH of the system be within the range of 3 to 11. A pH of 4 to 7 is preferred. Typical reaction temperatures and times are illustrated hereafter in Table 1.

A preferred method for introducing amidopropylphosphinic groups into the acrylic acid polymers or co-polymers thereof with acrylamide is to react these polymers with allyl amine to produce the corresponding allyl amides. These polymers containing the allyl amide groups are then reacted with alkali metal hypophosphites in accordance with U.S. Pat. No. 4,590,014.

The preparation of the phosphinate-modified polymers is illustrated in Table 1. In Table 1 PAA and AA are polyacrylic acid and acrylic acid respectively, AAm is acrylamide, MAA is methacrylic acid and VAc is vinyl acetate.

TABLE 1

GENERAL PROCEDURE FOR MODIFICATION: A mixture of the amine and the polymer solution were sealed in a reaction vessel capable of withstanding a pressurized chemical reaction and then heated to the specified temperature for the specified reaction time.

| SAMPLE | POLYMER COMPOSITION | MOL. Wt. | AMINOALKYL PHOSPHINIC ACID | MOL % CHARGE AMINE | RXN. TEMP. | RXN. TIME | RXN. pH |
|---|---|---|---|---|---|---|---|
| A | PAA | 4500 | $H_2NCH_2CH(OH)(PO_2H_2)$ | 5 | 150° C. | 5 HRS. | 9.0 |
| B | PAA | 4500 | $H_2NCH_2CH(OH)(PO_2H_2)$ | 15 | 150° C. | 5 HRS. | 6.3 |
| C | 50/50 AA/AAm | 6450 | $H_2NCH_2CH(OH)(PO_2H_2)$ | 10 | 150° C. | 5 HRS. | 6.5 |
| D | 50/30/20 AA/AAm/MAA | 11,200 | $H_2NCH_2CH(OH)(PO_2H_2)$ | 10 | 150° C. | 5 HRS. | 4.0 |
| E | 45/50/5 AA/AAm/VAc | 7050 | $N_2NCH_2CH(OH)(PO_2H_2)$ | 10 | 150° C. | 5 HRS. | 3.7 |
| F | PAA | 5400 | $H_2NCH_2C(CH_3)(OH)PO_2H_2$ | 10 | 140° C. | 8 HRS. | 3.7 |
| G | 50/50/ AA/AAm | 2500 | $H_2NCH_2C(CH_3)(OH)PO_2H_2$ | 25 | 140° C. | 8 HRS. | 4.8 |
| H | PAA | 5400 | $H_2NCH_2CH=CH_2$ | 10 | 140° C. | 12 HRS. | 3.8 |
| I | 50/50 AA/AAm | 2500 | $H_2NCH_2CH=CH_2$ | 25 | 140° C. | 12 HRS. | 4.9 |
| J | AAm | — | $NH_2CH_2CH_2CH_2(PO_2H_2)$ | 10 | 140° C. | 6 HRS. | 5.4 |

We claim:

1. Acrylamide homopolymers, acrylic acid homopolymer and co-polymers of acrylic acid with acrylamide having a molecular weight within the range of 1,000-100,000 which have been modified to contain up to about 50 mole percent of amido($C_2$-$C_6$ alkyl)phosphinic acid groups and the alkali metal, ammonium and amine salts thereof.

2. Acrylamide homopolymers, acrylic acid homopolymers and copolymers of acrylic acid with acrylamide having a molecular weight within the range of 1,000-100,000 which have been modified to contain up to about 30 mole percent of amido($C_2$-$C_6$ alkyl)phosphinic acid groups and the alkali metal, ammonium and amine salts thereof.

3. The acrylamide homopolymers and copolymers of claim 2 where the amido($C_2$-$C_6$ alkyl)phosphinic acid groups are from the group consisting of alpha-hydroxy-beta-amidoethylphosphinic acid, alpha-hydroxy-beta-amidoisopropylphosphinic acid and amidopropylphosphinic acid.

4. The acrylamide homopolymers and copolymers of claim 3 where the amido($C_2$-$C_6$ alkyl)phosphinic acid group is alpha-hydroxy-beta-amidoethylphosphinic acid.

5. The acrylamide homopolymers and copolymers of claim 3 where the amido($C_2$-$C_6$ alkyl)phosphinic acid group is alpha-hydroxy-beta-amidoisopropylphosphinic acid.

6. The acrylamide homopolymers and copolymers of claim 3 where the amido($C_2$-$C_6$ alkyl)phosphinic acid group is amidopropylphosphinic acid.

* * * * *